United States Patent
Suchánek et al.

(10) Patent No.: US 9,084,750 B2
(45) Date of Patent: Jul. 21, 2015

(54) **ANTIFUNGAL MIXTURE WITH FUNGAL ORGANISM *PYTHIUM OLIGANDRUM***

(71) Applicants: Martin Suchánek, Prague (CZ); Radim Klimeš, Prague (CZ)

(72) Inventors: Martin Suchánek, Prague (CZ); Radim Klimeš, Prague (CZ)

(73) Assignee: Bio Agens Research and Development-Bard, s.r.o., Cerncice (CZ)

( * ) Notice: Subject to any disclaimer, the term of this patent is extended or adjusted under 35 U.S.C. 154(b) by 0 days.

(21) Appl. No.: 14/152,554

(22) Filed: Jan. 10, 2014

(65) Prior Publication Data

US 2014/0127167 A1     May 8, 2014

Related U.S. Application Data

(63) Continuation of application No. 13/505,788, filed on May 3, 2012, now abandoned.

(30) Foreign Application Priority Data

Nov. 4, 2009    (CZ) .................................. 2009-724

(51) Int. Cl.
    *A01N 63/04*     (2006.01)
    *A61K 36/06*     (2006.01)

(52) U.S. Cl.
    CPC ................ *A61K 36/06* (2013.01); *A01N 63/04* (2013.01)

(58) Field of Classification Search
    CPC .............................. A01N 63/04; A61K 36/06
    See application file for complete search history.

(56) References Cited

U.S. PATENT DOCUMENTS 4,259,317 A   *   3/1981   Vesely et al. ................. 424/93.5

OTHER PUBLICATIONS

Horakova, "Cannibal" fungus helps treat skin diseases including psoriasis, Radio Prague, Jul. 20, 2004.*

* cited by examiner

*Primary Examiner* — Karen Cochrane Carlson
*Assistant Examiner* — Jennifer M. H. Tichy
(74) *Attorney, Agent, or Firm* — Dykema Gossett PLLC

(57) ABSTRACT

The antifungal mixture is designed for fighting human diseases and animal diseases of fungal, bacterial or other origin and for violation of bio-films on heterogeneous materials used both in human and veterinary medicine and for elimination of microflora from various objects coming in contact with humans or animals. The antifungal mixture uses the active component of the fungal organism *Pythium oligandrum* in the mixture with inert components; the said antifungal mixture contains 0.001 to 25 weight portions of the fungal organism *Pythium oligandrum* and 75 to 99.999 weight portions of inert components. The activity of the fungal organism *Pythium oligandrum* in the mixture arises at the moment when this organism gets in touch with humidity.

2 Claims, No Drawings

ANTIFUNGAL MIXTURE WITH FUNGAL ORGANISM *PYTHIUM OLIGANDRUM*

CROSS-REFERENCE TO RELATED APPLICATIONS

This application is a continuation of U.S. patent application Ser. No. 13/505,788, filed May 3, 2012, now abandoned, which was a U.S. national stage of PCT/CZ2009/000154, filed 14 Dec. 2009, which derived from Czech Application PV 2009-724, filed 4 Nov. 2009. All priorities are requested.

FIELD OF THE INVENTION

The invention relates to an antifungal mixture with fungal organism *Pythium oligandrum* designed for fighting fungi including fungal diseases and bacteria.

BACKGROUND OF THE INVENTION

Fungi and fungal diseases are a problem of every society and especially fungal diseases of skin of both people and animals belong to frequently occurring diseases of people and animals. Such fungal diseases are even more serious because they are usually transmitted not only by a direct contact of the sick and the healthy but also through the objects, which were in contact with the source of infection.

The treatment of such dermatological diseases is very difficult and lengthy and nowadays, the treatment methods are based especially on the application of system antimycotics, exceptionally also chemotherapy, which means that aggressive forms of treatment with chemical therapeutics are used against pathogenic microorganisms, which cause the diseases; however, they usually impact not only the targeted pathogen but also the tissues of the recipient of the therapeutics. Other aggressive forms of treatment with antibiotics and hormones have contraindication, too.

The said conservative types of treatment are often completed with cosmetic preparations, which are, however, based on the application of chemistry again, even though there are also natural cosmetic preparations, the basic source of which are substances of both floral and animal origin, including some inorganic substances occurring in nature (salts etc.).

Only recently, dermatological troubles have started to be approached differentially and in a complex way and sensitive natural methods have been used preferentially more and more. Such methods also include e.g. the application of the fungus *Pythium oligandrum* according to the document CZ 9883 U1 in the form of the biological preparation for fighting the origins of dermatophysis, which includes the said fungal organism in the form of oospora as the effective substance, when the total number of oospora is $2\times10^5$ in 1 g of the preparation as a maximum. However, this solution has a limited range of application and its effective substance is only bound on the inorganic carrier, which is silicon dioxide.

Fungi from was and fungi, yeast fungi and bacteria from various objects are removed by means of a series of different preparations, which are, however, never based on the application of the effective substance of the fungal organism *Pythium oligandrum*.

SUMMARY OF THE INVENTION

The above mentioned disadvantages of the current solutions are eliminated to a certain extent with the antifungal mixture with the fungal organism *Pythium oligandrum* according to the invention, where the effective substance of the fungal organism is used in higher concentrations and with the application of new components of the final mixtures and newly also zoospore and zoosporangia and enzymes.

The fungal organism *Pythium oligandrum* from the kingdom Chromista-Stramenopila is a strong mycoparasite; it parasites over 20 families of causative agents of fungal diseases and represents the dividing line between fungi and protozoa because of its sexual as well as asexual reproduction. The fibres of *Pythium oligandrum* penetrate the cells of the parasite (fungi, yeast fungi, bacteria) and draw the substances required for its own nutrition from them. On the basis of nutrition and spatial competition, it squeezes out the pathogens from the spaces. The nature of the activity of this fungus is, therefore, parasiting on fungi with the simultaneous production of enzymes, which further increase the efficiency of the fungus. It can be said that *Pythium oligandrum* attacks the opponent with direct parasitism. After the achievement of the task, i.e., exhaustion of the parasite, *Pythium oligandrum* disappears from that locality (both human and animal bodies do not represent a natural environment for it and it cannot adapt to such environment) and it gives way for the re-settlement of the so-called normal micro-flora or, unless it finds new nutrition (fungi), it is encapsulated into dormancy conditions and its life cycle is paused.

It has been newly detected that for suppressing fungal diseases and their symptoms, it is more advantageous to use higher concentrations of the effective substance, i.e., reproduction organs, than $2\times10^5$ in 1 g of the mixture. Further to that, *Pythium oligandrum* can be used independently or in combination with other carriers (components) than silicon dioxide, which is also used according to the aforesaid applied design.

Higher concentrations of the effective substance can be achieved by the is application of other reproduction organs of the fungal organism *Pythium oligandrum* than only oospore. The number of the reproduction organs of the fungal organism *Pythium oligandrum* according to this technical solution is higher than $2\times10^5$ in 1 g of the mixture. In terms of the weight expression, it means that the mixture consists of 0.001 to 25 weight portions of *Pythia oligandrum* as a minimum and 75 to 99.999 weights portions of inert components.

A new finding also concerns other mechanisms of the effect. Many diseases are caused by the presence of bacteria. With its metabolism, *Pythium oligandrum* produces various enzymes used for the decomposition of host organisms. Such enzymes also represent unfavourable environment for bacteria and, at the same time, the presence of bacteria in the affected organs is supported by the occurrence of microscopic fungi producing nutrition components that are important to the bacterial development. *Pythium oligandrum* can parasite on such microscopic fungi and, thereby violate the environment suitable for the propagation of pathogenic bacteria. The combination of both factors results in the suppression of reproduction of bacteria, which cease in causing the putrefactive processes. In the same way, the bio-films are violated, which could cause diseases of the urinary system and, in case of occurrence on teeth, gingivitis or contaminate heterogeneous materials used in various treatment methods.

Surprisingly it was detected that *Pythium oligandrum* also suppresses symptoms of other diseases than dermatophysis, namely also microbiological settlement of proboscis, other inflammations of buccal caxity, psoriasis, hemorrhoids, varicose ulcers, bed sores, "diabetic feet", atopic eczema, acne, cold sores, sore spots, nail fungi, falling hair, dandruff or old-age itchiness. In the veterinary section, this solution can be newly used for suppressing mycotic infections and putrefactive processes on paws, cloven hoofs, hoofs, hair, skin, eyes, shells, in mouth, scales, mucous membranes and auditory passages of animals or in the body of animals.

Therefore, this new solution enables to use the mixture for the treatment of human diseases of fungal, bacterial or other origin on skin, mucous membranes, in the hair part or in the body of humans. Further to that, this solution enables to use the mixtures for animals against the diseases of fungal, bacterial or other origin on paws, cloven hoofs, hoofs, hair, skin, eyes, shells, in mouth, scales, mucous membranes and auditory passages of animals or in the body of animals.

Another application is also the violation of bio-films on heterogeneous materials used both in human and veterinary medicine (artificial valves, joint replacements, contact lenses, catheters, etc.). The technical solution also enables to eliminate microflora virtually from all objects, which come into contact with humans and animals, e.g., from interiors of the means of transport, seat furniture, animal cages etc.

The above mentioned new applications of the fungal organism *Pythium oligandrum* are also enabled by the new application of other components forming the mixture. New mixtures were examined and selected because of better, more understandable and more comfortable application of the preparation for the consumer so that their possible preparation for application and the actual application were dear, simple and comfortable and corresponded to the common habits in the twenty first century. At the same time, they shall also comply with the requirements for the purpose of application. Various inert carriers are used for the new mixtures in different ratios, which do not damage the microscopic fungus *Pythium oligandrum* (creation of the fungal fibres and characteristic echinate oospore, zoospore and zoosporangia) and producing various enzymes, which are collectively called oligandrin.

*Pythium oligandrum* is used in various concentrations for these new mixtures, when the number of the reproductive organs of the fungal organism *Pythium oligandrum* is higher than $2 \times 10^5$ in 1 g of the mixture.

The new inert components are especially biological organic and/or inorganic solutions, such as oil bases, physiological solutions, aromatic solutions, ointments, suppositories, pastes, creams, toothpastes, mouthwashes etc. Further to that, it concerns suspensions, emulsions or solid (loose) compositions of individual components, e.g. dusting powders, powders, etc. or suspensions, emulsions or solutions from such individual substances. In terms of weight expression, as stated above, it means that the mixture includes 0.001 to 25 weight portions of *Pythium oligandrum* and 75 to 99.999 weight portions of inert components.

The activity of *Pythium oligandrum* in the mixture only arises after soaking or wetting, e.g., also by skin, which is always sweating, etc.

EXAMPLES

In all Cases, it Concerns % Representation of Weight Portions

Example No. 1

Mixture for Suppressing Aphthae and Parodontosis

| | |
|---|---|
| *Pythium oligandrum* | 10.1% |
| Inert component | 8.9% |
| | of which |
| Citric acid | 33.3% |
| Sodium carbonate | 2.6% |
| Spearmint aroma | 0.45% |
| Sorbitol | 23.45% |
| Sodium acid carbonate | 26.79% |
| Polyethylene glycol 6000 | 3.34% |

Example No. 2

Mixture for Suppressing Atopic Eczema

| | |
|---|---|
| *Pythium oligandrum* | 0.5% |
| Inert component | 99.5% |
| | of which |
| Residue of dried organic cultivation medium approx. | 9.5% |
| Refined olive oil | 85.09% |
| Colloid silicon dioxide (Aerosil 200) | 4.8% |
| Vitamin E (Covi ox T 70) | 0.08% |
| *Eucalyptus* oil | 0.03% |

Example No. 3

Mixture for Softening Dry Skin in Case of Diabetes

| | |
|---|---|
| *Pythium oligandrum* | 1.72% |
| Inert component | 98.28% |
| | of which |
| Residue of dried organic cultivation medium approx. | 30.5% |
| Refined almond oil | 61.37% |
| Aerosol 200 | 6.30% |
| Sea buckthorn oil | 1.65% |
| Vitamin E (Covi ox T 70) | 0.08% |
| Balm oil | 0.03% |

Example No. 4

Mixture for Suppressing Symptoms of Psoriasis

| | |
|---|---|
| *Pythium oligandrum* | 0.25-0.5% |
| Inert component | 99.75-99.5% |
| | of which |
| Residue of dried organic cultivation medium approx. | 4.75-9.5% |
| Shea butter BIO (BIO *Butyrospermum Partii* Butter) | 34.5% |
| Sunflower oil BIO (BIO *Helianthus Annuus* Seed Oil) | 34.5% |
| Beeswax (Cera Alba) | 1% |
| Silica sand (Oxidum silicii) | 10-15% |

Example No. 5

Mixture for Suppressing Microbial Settlement of Auditory Passage of Animals

| | |
|---|---|
| *Pythium oligandrum* | 25.0% |
| Inert component | 75.0% |
| | of which |
| Refined olive oil | 27.5% |
| Shea butter (Cetiol SB 45) | 22.0% |
| Fish oil with vitamin E | 18.5% |

| | |
|---|---|
| Glycerol monostearate (*Cutina* GMS V) | 2.6% |
| Sea buckthorn oil | 3.3% |
| Covi ox T 70 | 1.1% |

FIELD OF APPLICATION

The antifungal mixture with fungal organism *Pythium oligandrum* can be used both in human and veterinary medicine, in the cosmetic industry and also in households for maintaining cleanness and for elimination of fungi from walls of building objects and for violation of bio-films on heterogeneous materials and for elimination of microflora on objects coming in contact with humans or animals.

The invention claimed is:

1. A method for treating human or animal mucous surfaces which exhibit periodontitis and tongue aphthae comprising the steps of:
   (a) providing a composition comprising a mixture of between 0.001 weight percent and 25 weight percent of *Pythium oligandrum* and between 99.999 weight percent and 75 weight percent of an inert carrier, said composition containing fungal fibres, echinate oospores, zoospores, zoosporangia and active enzymes, the composition containing a number of reproductive organs of *Pythium oligandrum* higher than $2\times10^5$ in a gram of the composition, and
   (b) applying an effective amount of said composition on said human or animal mucous surfaces which exhibit periodontitis and tongue aphthae.

2. A method for treating fungal or bacterial biofilms on materials, devices and instruments used in human or veterinary medicine, comprising the steps of:
   (a) providing a composition comprising a mixture of between 0.001 weight percent and 25 weight percent of *Pythium oligandrum* and between 99.999 weight percent and 75 weight percent of an inert carrier, said composition containing fungal fibres, echinate oospores, zoospores, zoosporangia and active enzymes, the number of reproductive organs of *Pythium oligandrum* higher than $2\times10^5$ in a gram of the composition, and
   (b) applying an effective amount of said composition on said fungal or bacterial biofilms.

\* \* \* \* \*